United States Patent [19]

Niazy et al.

[11] Patent Number: 6,082,177
[45] Date of Patent: Jul. 4, 2000

[54] NITRIC OXIDE ENHANCED RESPONSE CIRCUIT FOR GAS ANALYZER

[75] Inventors: Jeffrey W. Niazy, Lindenhurst, Ill.; Christiaan Hoede, EJ Diemen, Netherlands; Robert J. Capiga, Hoffman Estates, Ill.

[73] Assignee: Snap-on Tools Company, Kenosha, Wis.

[21] Appl. No.: 09/150,685

[22] Filed: Sep. 10, 1998

Related U.S. Application Data

[60] Provisional application No. 60/059,523, Sep. 22, 1997.

[51] Int. Cl.[7] ............................................... G01N 27/416
[52] U.S. Cl. .......................................................... 73/23.31
[58] Field of Search .................................... 73/23.31, 23.3

[56] References Cited

U.S. PATENT DOCUMENTS

| | | |
|---|---|---|
| 3,636,463 | 1/1972 | Ongkiehong . |
| 3,696,247 | 10/1972 | McIntosh et al. ...................... 73/23.31 |
| 4,018,198 | 4/1977 | Williams . |
| 4,060,714 | 11/1977 | Lappington et al. . |
| 4,233,033 | 11/1980 | Eifler et al. . |
| 4,250,856 | 2/1981 | Abbey ...................................... 123/439 |
| 4,252,098 | 2/1981 | Tomczak et al. . |
| 4,258,563 | 3/1981 | Yasuda et al. . |
| 4,357,577 | 11/1982 | Smither . |
| 4,463,594 | 8/1984 | Raff et al. . |
| 4,494,399 | 1/1985 | Youngman . |
| 4,519,237 | 5/1985 | Kubo . |
| 4,534,330 | 8/1985 | Osuga et al. . |
| 4,538,573 | 9/1985 | Merrick . |
| 4,707,242 | 11/1987 | Schneider et al. . |
| 4,725,148 | 2/1988 | Endo et al. . |
| 4,758,740 | 7/1988 | Wilhelm et al. . |
| 4,901,006 | 2/1990 | Harrison et al. . |
| 5,255,554 | 10/1993 | Mallebrein et al. . |
| 5,323,635 | 6/1994 | Ueno et al. . |
| 5,337,234 | 8/1994 | Anderson et al. . |
| 5,542,285 | 8/1996 | Merilainen et al. . |
| 5,596,975 | 1/1997 | Thomas et al. . |
| 5,606,284 | 2/1997 | Tamesue et al. . |
| 5,625,320 | 4/1997 | Hagerty . |
| 5,675,069 | 10/1997 | Schleupen et al. . |
| 5,810,984 | 9/1998 | Kudo et al. . |

*Primary Examiner*—Daniel S. Larkin
*Attorney, Agent, or Firm*—Seyfarth, Shaw, Fairweather & Geraldson

[57] ABSTRACT

An exhaust emissions analyzer for an automotive internal combustion engine has sensors for detecting constituents of the exhaust emissions, including a nitric oxide cell which receives the emissions and outputs an electrical signal indicative of nitric oxide in the emissions. An R-C circuit is interposed between the output of the nitric oxide cell and processing circuitry for enhancing the response time of the nitric oxide cell, reducing the rise and fall times of the cell output of signal. A temperature-responsive switching circuit disconnects the R-C enhancement circuit above a predetermined ambient temperature.

17 Claims, 3 Drawing Sheets

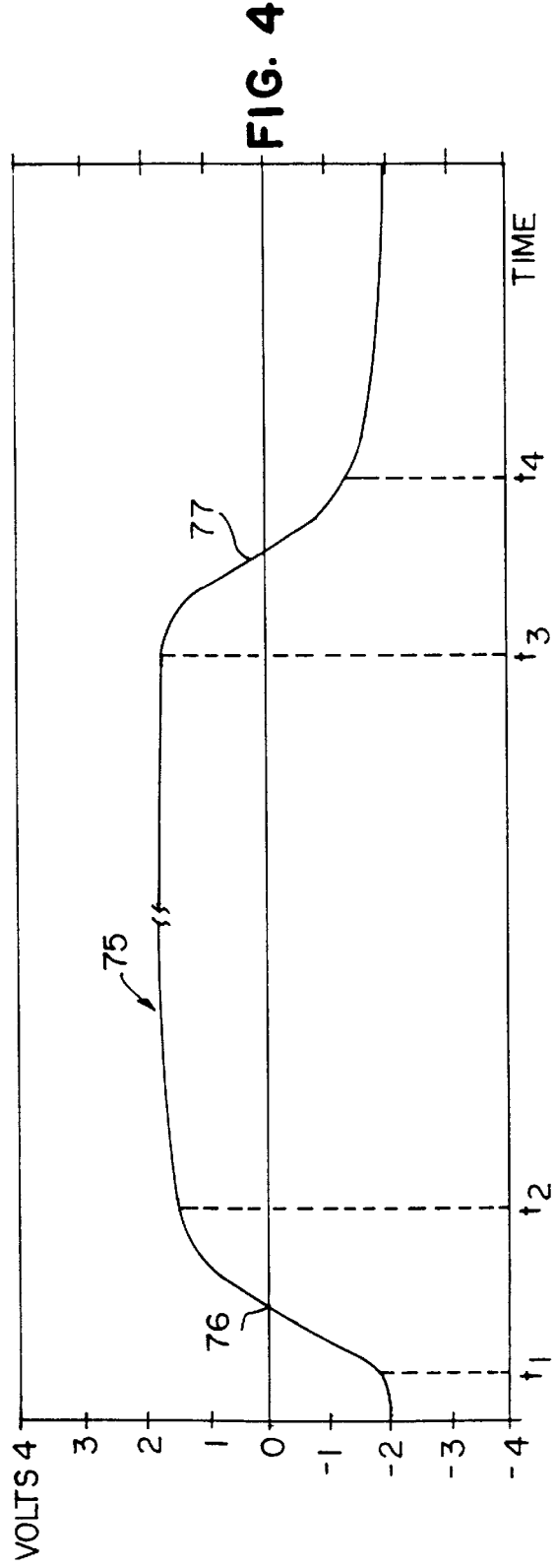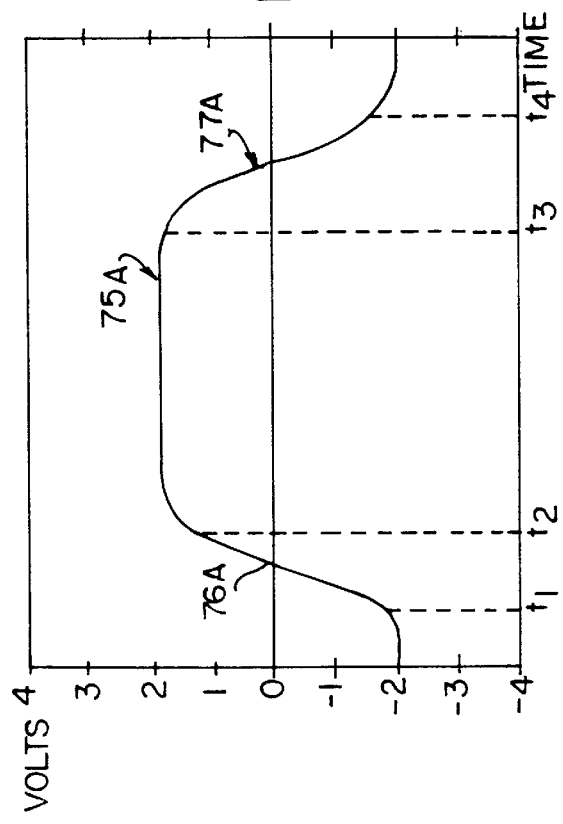

NITRIC OXIDE ENHANCED RESPONSE CIRCUIT FOR GAS ANALYZER

CROSS-REFERENCE TO RELATED APPLICATION

This application claims the benefit of U.S. provisional application Ser. No. 60/059,523, filed Sep. 22, 1997.

BACKGROUND OF THE INVENTION

The present invention relates generally to test and diagnostic equipment for testing motor vehicles, particularly vehicles powered by internal combustion engines. The invention has particular application to diagnostic equipment incorporating gas analyzers for analyzing exhaust emissions from internal combustion engines, and even more specifically to nitric oxide (NO) sensor circuits for such gas analyzers.

The present invention is an improvement of a NO sensing circuit of the type used with a diagnostic system, such as that sold by Sun Electric and known as a Service Inspection System. That system includes an infrared (IR) shelf assembly module, which includes a non-dispersive infrared (NDIR) optical bench which detects the concentration of hydrocarbons, carbon monoxide, carbon dioxide and other gases within the vehicle exhaust system. The NDIR optical bench includes optional input/output circuits and peripheral transducers for additional inputs, including a NO input.

There are government regulations setting forth specifications for the performance of engine diagnostic equipment and, in particular, emissions analyzers. Among these specifications is a response time specification for certain gas constituent sensors. The specifications essentially require that the sensor output reach a certain percentage of a nominal output reading within a certain time period, e.g., within four or five seconds, the specified time period varying with the ambient temperature at which the test is conducted. Applicants have found that when the NO sensor was utilized in an emissions analyzer, its response times, i.e., the rise and fall times of the sensor output, could exceed the specifications set by government regulations, particularly at low ambient temperatures. Applicants attempted heating the NO sensing cell, as with a resistive heater, but the heater did not decrease response times enough to meet specifications.

SUMMARY OF THE INVENTION

It is a general object of the present invention to provide an improved fluid constituent detection apparatus which avoids the disadvantages of prior apparatus while affording additional structural and operating advantages.

An important feature of the invention is the provision of a sensing circuit for a gas constituent which provides relatively fast response times.

In connection with the foregoing feature, another feature of the invention is the provision of a sensing circuit of the type set forth, which does not require any auxiliary heating.

Still another feature of the invention is the provision of a sensing circuit of the type set forth which is temperature responsive, so as to alter operation of the circuit depending upon ambient temperature.

Certain ones of these and other features of the invention may be attained by providing apparatus for analyzing exhaust emissions from an internal combustion engine comprising: a transducer assembly including a sensor responsive to nitric oxide in the emissions for generating an electrical output signal, a processor, and a response enhancing circuit adapted to be coupled between the transducer assembly and the processor for reducing the response time of the analyzing apparatus.

Other features of the invention may be attained by providing fluid constituent detection apparatus comprising: a transducer responsive to a predetermined constituent of a fluid for generating an electrical output signal, a response enhancing circuit adapted to be coupled to the transducer for reducing the response time of the detection apparatus, and a switch mechanism having a first condition for electrically connecting the response enhancing circuit to the transducer and a second condition for electrically disconnecting the response enhancing circuit from the transducer.

Still other features of the invention may be attained by providing a method for sensing a constituent gas in the exhaust emissions of an internal combustion engine, comprising: exposing the emissions to a constituent transducer for producing an electrical output signal indicative of the presence of the constituent gas, sensing the ambient temperature, and enhancing the output of the transducer only below a predetermined ambient temperature.

The invention consists of certain novel features and a combination of parts hereinafter fully described and illustrated in the accompanying drawings, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIGS. 4 and 5 are graphs illustrating the effect of the response control circuit of FIG. 3.

DESCRIPTION OF THE PREFERRED EMBODIMENT

Figure 1:
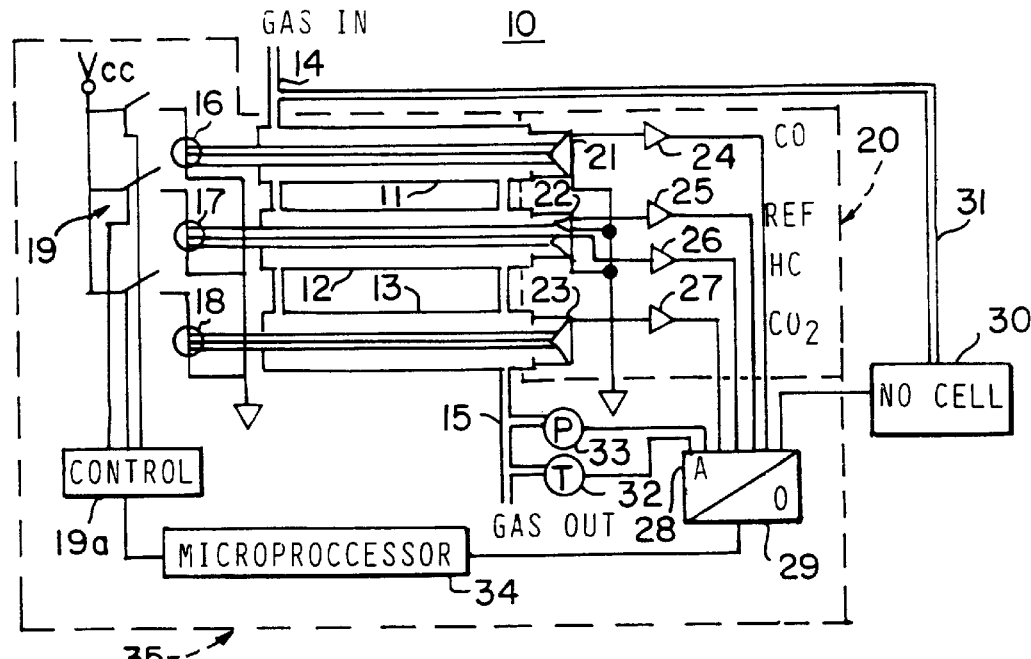
FIG. 1 is a partially schematic and partially functional block diagrammatic view of a gas analyzer for a service inspection system of the type with which the present invention is intended to be used.

Referring to FIG. 1 there is illustrated a sensor or transducer assembly of a prior art exhaust analyzer 10 of the type with which the present invention is intended to be used, including an optical IR bench 35 and a nitric oxide cell 30, which is an electrochemical cell transducer or sensor and produces an electrical output indicative of the amount of nitric oxide in the gas sample.

More specifically, the optical IR bench 35 includes gas sample tubes 11, 12, and 13 which may, respectively, be designed for sensing carbon monoxide (CO), hydrocarbons (HC), and carbon dioxide ($CO_2$). The sample tube 12 communicates with each of the other sample tubes 11 and 13, and the sample tube 11 also communicates with a gas inlet conduit 14, which is adapted to be coupled to receive the exhaust emissions from an associated internal combustion engine (not shown) under test, while the sample tube 13 is coupled to a gas outlet conduit 15. The sample tubes 11–13 are, respectively, provided with infrared (IR) sources 16–18, respectively located at one end of the tubes 11–13 for radiating infrared energy through the tubes, the sources 16–18 being coupled to an associated DC voltage source $V_{cc}$ through a switch assembly 19 operated by a switch control circuit 19a. Preferably, the IR sources 16–18 are duty cycle controlled (chopped) to provide an ON/OFF reference state for each IR sensor. The optical IR bench 35 also includes an optical filter/detector assembly 20, which includes three detectors 21, 22, and 23, respectively provided at the ends of the sample tubes 11–13 opposite the IR sources 16–18, and four associated optical filters 24–27. More particularly, the CO and $CO_2$ sample tubes 11 and 13, respectively, have optical filters 24 and 27, while the HC sample tube 12 has two optical filters, a reference filter 25 and an HC filter 26.

It will be appreciated that the gases inside the sample tubes 11–13 absorb the IR energy as it passes therethrough, and the detectors convert the received IR energy into a voltage output signal, which is chopped because the input voltage to the IR sources is chopped. The outputs of the optical filters 24–27 are applied through an amplifier circuit 28 and, after digital conversion at 29, are applied to a microprocessor 34 which analyzes the output signals and also controls the switch control circuit 19a. The output of the NO cell 30 is also provided to the amplifier circuit 28 of the optical IR bench 35.

Figure 2:
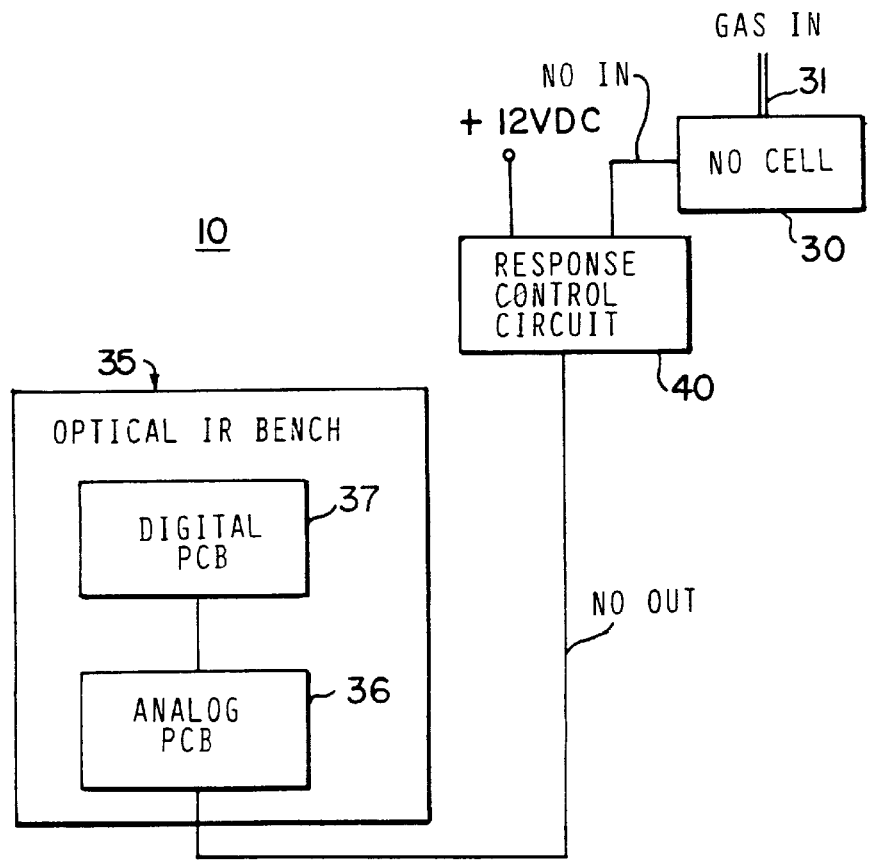
FIG. 2 is a block diagram of a pertinent portion of the gas analyzer of FIG. 1, illustrating the location of the sensor response control circuit of the present invention.
Figure 3:
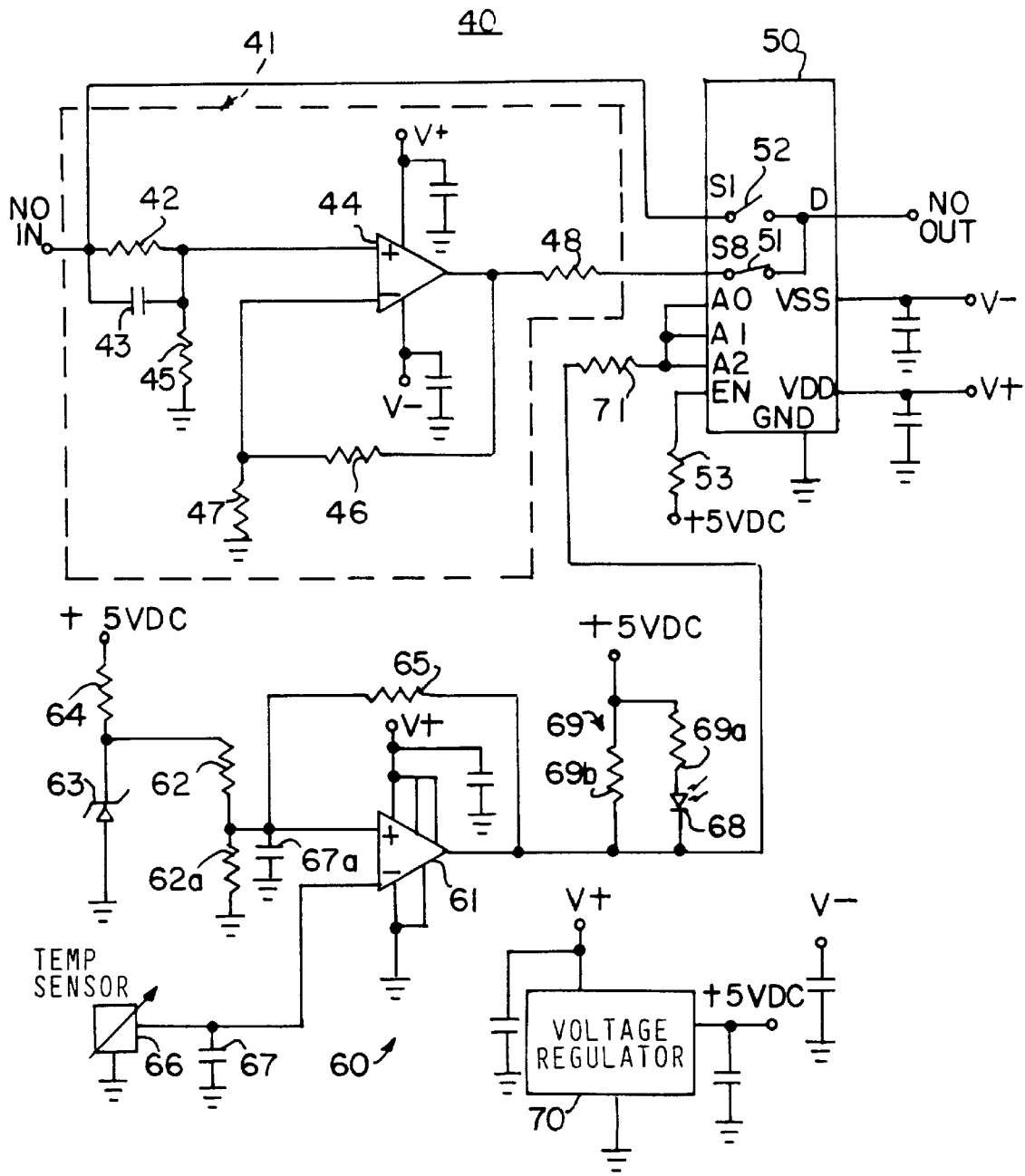
FIG. 3 is a schematic diagram of the sensor response control circuit of the present invention.

It is a fundamental aspect of the present invention that a response control circuit 40 is interposed between the NO cell 30 and the optical IR bench 35, as shown in FIG. 2. The details of the response control circuit 40 are shown in FIG. 3. The NO cell 30 has an inlet conduit 31, which communicates with the gas inlet conduit 14, and generates an electrical output signal indicative of the presence of a nitric oxide constituent in the inlet emissions gases, which output is also applied to the amplifier circuit 28 as signal "NO IN". The NDIR optical bench 35 also includes a temperature sensor 32 and a pressure sensor 33 coupled to the gas outlet conduit 15 and producing electrical output signals which, are in turn, coupled to the amplifier circuit 28. Preferably, the amplifier circuit 28 and the switch control circuit 19a are located on an analog printed circuit board 36, while the analog-to-digital conversion circuitry 29 and the microprocessor 34 are located on a digital printed circuit board 37. In accordance with the present invention, the NO IN signal from the NO cell 30 is applied to the response control circuit 40, the output of which, designated "NO OUT" is applied to the amplifier circuit 28 on the analog PCB 36.

Referring to FIG. 3, the response control circuit 40 includes a response-enhancing circuit 41. In particular, the NO IN signal from the NO cell 30, is applied through a parallel R-C circuit, including a resistor 42 and a capacitor 43, to the non-inverting input of an operational amplifier (op amp) 44, which may be a TLC252C, which input is also connected through a resistor 45 to ground. The output of the op amp 44 is connected through a resistor 46 to its inverting input, which input is also connected through a resistor 47 to ground. The output of the op amp 44 is also connected through a resistor 48 to one input (S8) of an analog multiplexer 50, which may be a ADG508A. The NO IN signal is also connected directly to the S1 input of the multiplexer 50, these two inputs being respectively connected to the NO OUT terminal D of the multiplexer 50 through normally-open switch paths 51 and 52, the selection of which path is closed being determined by the signals on the A0, A1, and A2 inputs. The multiplexer 50 also has an enable input connected through a resistor 53 to a +5 VDC supply and VSS and VDD inputs respectively connected to V− and V+ supplies.

Thus, it will be appreciated that the R-C circuit provided by the resistor 42 and capacitor 43 is normally connected to the NO OUT output. In operation, the R-C circuit provides a time constant and the resistor 42 cooperates with the resistor 45 to provide a voltage divider, this circuitry serving to reduce the rise and fall times of the response of the NO cell 30. Because of the reduction of voltage at the input of the op amp 44 by reason of the voltage divider, the op amp 44 cooperates with the resistors 46 and 47 to provide a suitable amplification, preferably about 1.15.

A temperature-responsive control circuit 60 for the multiplexer 50 includes an op amp 61, which may be an LM311, configured as a comparator, which has its non-inverting input connected to the junction between resistors 62 and 62A of a voltage divider, which is connected between ground and the cathode of a Zener diode 63, the anode of which is grounded. The cathode of the Zener diode 63 is also connected through a resistor 64 to the +5 VDC supply. The output of the comparator op amp 61 is connected to its non-inverting input through a resistor 65. The resistor 62 sets a reference voltage level corresponding to a predetermined ambient temperature level, which may be about 80° F. The inverting input of the comparator 61 is connected to a temperature sensor 66, which senses the ambient temperature and outputs an electrical signal indicative of that temperature. The inverting and non-inverting inputs of the op amp 61 are also respectively connected to ground through filter capacitors 67 and 67a.

When the sensed ambient temperature exceeds the reference temperature level, the comparator switches to produce an output signal, applied through a resistor 71 to the A0, A1, and A2 inputs of the multiplexer 50 to switch its condition, thereby opening the path 51 and closing the path 52 so that the NO IN signal is connected directly to the NO OUT terminal, thus effectively removing the response-enhancing circuit 41 from the circuit. This switching will also be visually indicated by illumination of an LED 68, which is powered from a +5 VDC supply through a voltage divider 69 provided by resistors 69a and 69b. The +5 VDC supply is obtained from a voltage regulator 70, which may be an LM7805. The V+ and V− supply voltages are provided from an external source and are applied to the op amp 44 and to the multiplexer 50, and the V+ supply is applied to the op amp 61, all of these supplies being provided with suitable bypass capacitors.

In operation, the R-C response-enhancing circuit 41 serves to reduce the rise and fall times of the response of the NO cell 30 to levels well within the specifications provided by pertinent government regulations. However, it has been found that, at ambient temperatures above a certain level, typically approximately 80° F., the response time enhancement provided by the R-C network is unnecessary and, indeed, may result in overshoot of the intended output voltage level of the sensor circuitry. Thus, the control circuit 60 serves to automatically remove the R-C network from the response control circuit 40 when the ambient temperature reaches the predetermined temperature level and will, likewise, switch it back into the circuit when the ambient temperature falls below that predetermined level.

Referring now to FIG. 4, there is illustrated a waveform 75 representative of the response of the NO cell 30 without the enhancement circuit of the present invention. The waveform 75 has a rising portion 76, which rises from an initial value of −2 volts to a maximum output value of approximately +1.8 volts, i.e., a total rise of 3.8 volts. Similarly, after disconnection from the exhaust emissions, the response falls back to the initial zero-emissions level during a fall period 77 of the waveform. The rise time of the waveform 75 is calculated as the time required to rise from the essentially zero-emissions starting point to 90% of the maximum output value, while the fall time is the time required to drop from the maximum output value to approximately 10% of that value. The rise time is indicated in FIG. 4 as the time from t1 to t2, which was calculated to be 5.072 seconds, while the fall time from t3 to t4 was calculated at 5.576 seconds, with all measurements taken at 40° F.

Referring to FIG. 5, there is illustrated the corresponding waveform 75A utilizing the response-enhancing circuit of the present invention. In this case, the rising portion 76A of the waveform has a rise time from t1 to t2 calculated at 2.416 seconds, while the falling portion 77A has a fall time from t3 to t4 calculated at 3.126 seconds. Thus, the response time of the NO cell has been nearly cut in half by the use of the present invention.

In a constructional model of the present invention, the op amp 44 may be a TLC252 CP, the comparator op amp 61 may be an LM311, the Zener diode 63 may be an LM336, the temperature sensor 66 may be an LM34C, and the voltage regulator 70 may be a 7805. It will be appreciated that the values of the resistors 42 and 45–48 and the capacitor 43 will vary depending upon the amount of speed-up of the NO cell response that is desired. Similarly, the values of the components of the control circuit 60 will vary depending upon the ambient temperature at which switching is desired.

From the foregoing, it can be seen that there has been provided gas sensor circuitry which provides an enhanced response time and automatically removes the enhancement when it is not needed.

While particular embodiments of the present invention have been shown and described, it will be obvious to those skilled in the art that changes and modifications may be made without departing from the invention in its broader aspects. The matter set forth in the foregoing description and accompanying drawings is offered by way of illustration only and not as a limitation.

We claim:

1. Apparatus for analyzing exhaust emissions from an internal combustion engine comprising:
    a transducer assembly including an electrochemical sensor responsive to an oxide of nitrogen in the emissions for generating an electrical output signal at an output,
    a processing circuit having an input and responsive to the output signal, and
    a response enhancing circuit adapted to be coupled in series between said output and said input for reducing the duration of said output signal, whereby the overall response time of the apparatus is reduced.

2. The apparatus of claim 1, and further comprising: a switch mechanism having a first condition electrically connecting said response enhancing circuit in series between said transducer assembly and said processing circuit and a second condition electrically disconnecting said response enhancing circuit from between said transducer assembly and said processing circuit and directly connecting said output to said input.

3. The apparatus of claim 2, and further comprising: an ambient condition sensor coupled to said switch mechanism for controlling the operation thereof.

4. The apparatus of claim 3, wherein said ambient condition sensor is a temperature sensor.

5. The apparatus of claim 2, and further comprising circuitry defining first and second parallel paths connected to said transducer assembly for receiving the output signal therefrom, said first path including said response-enhancing circuit, said switch mechanism in said first and second conditions thereof respectively connecting said first and second paths to said processor.

6. The apparatus of claim 1, wherein the response enhancing circuit includes an R-C circuit.

7. Fluid constituent detection apparatus having an output terminal and comprising:
    a transducer responsive to a predetermined constituent of a fluid for generating an electrical output signal at a transducer output,
    a response enhancing circuit adapted to be coupled to said transducer output for reducing the duration of the output signal, and
    a switch mechanism having a first condition for electrically connecting said response enhancing circuit in series between said transducer output and said output terminal and a second condition for electrically disconnecting said response enhancing circuit from said output terminal and connecting said transducer output directly to said output terminal.

8. The apparatus of claim 7, wherein the transducer includes a gas sensor responsive to a constituent gas.

9. The detector of claim 8, wherein the gas sensor is a nitric oxide cell.

10. The detector of claim 7, wherein the response enhancing circuit includes an R-C circuit.

11. The apparatus of claim 10, wherein the response enhancing circuit includes an amplifier.

12. The apparatus of claim 7, and further comprising circuitry defining first and second parallel paths connected to said transducer for receiving the output signal therefrom, said first path including said response enhancing circuit, and a processor, said switch mechanism in said first condition connecting said first path to said processor and in said second condition connecting said second path to said processor.

13. The apparatus of claim 7, and further comprising an ambient condition sensor coupled to said switch mechanism for controlling the operation thereof.

14. The apparatus of claim 13, wherein said ambient condition sensor is a temperature sensor.

15. A method for sensing a constituent gas in the exhaust emissions of an internal combustion engine comprising:
    exposing the emissions to a constituent transducer for producing an electrical output signal indicative of the presence of the constituent gas,
    sensing the ambient temperature, and
    reducing the duration of the output signal only when the ambient temperature is below a predetermined temperature.

16. The method of claim 15, wherein the constituent gas is nitric oxide.

17. The method of claim 16, wherein the enhancing includes passing the output signal through an R-C circuit.

* * * * *